United States Patent [19]
Dawson

[11] Patent Number: 5,442,175
[45] Date of Patent: Aug. 15, 1995

[54] GAS EVOLUTION COMPONENT ANALYSIS

[75] Inventor: Robert Dawson, Austin, Tex.

[73] Assignee: Advanced Micro Devices, Inc., Sunnyvale, Calif.

[21] Appl. No.: 315,094

[22] Filed: Sep. 29, 1994

[51] Int. Cl.$^6$ .............................................. H01J 49/04
[52] U.S. Cl. .................... 250/288; 250/282; 73/863.12; 73/864.83
[58] Field of Search .................. 250/288, 288 A, 282; 73/863.12, 864.83

[56] References Cited

U.S. PATENT DOCUMENTS 4,259,572  3/1981  Brunnee et al. ................ 250/288 A
5,191,211  3/1993  Gorman ............................ 250/288

OTHER PUBLICATIONS

McGee et al., The Review of Scientific Instruments, vol. 37, No. 5, May 1966, pp. 561-566.

*Primary Examiner*—Jack I. Berman
*Attorney, Agent, or Firm*—Conley, Rose & Tayon

[57] ABSTRACT

A method and apparatus for analyzing chemical compounds on a surface, such as the surface of a semiconductor wafer, comprising: a heater component for volatilizing the chemical compounds from the surface and capturing said volatilized compounds, a condensation surface having a hot end and a cold end and a thermal gradient therebetween, means for causing said volatilized chemical compounds to flow along said condensing surface so as to sequentially condense said chemical compounds and an exciter/analyzer for sequentially analyzing said condensed chemical compounds. The exciter/analyzer can comprise an ion beam, laser, or similar exciting device, coupled with a mass analyzer. The exciter/analyzer preferably scans the condensing surface from the hot end to the cold end and withdraws molecules for analysis as they are excited from the surface.

16 Claims, 1 Drawing Sheet

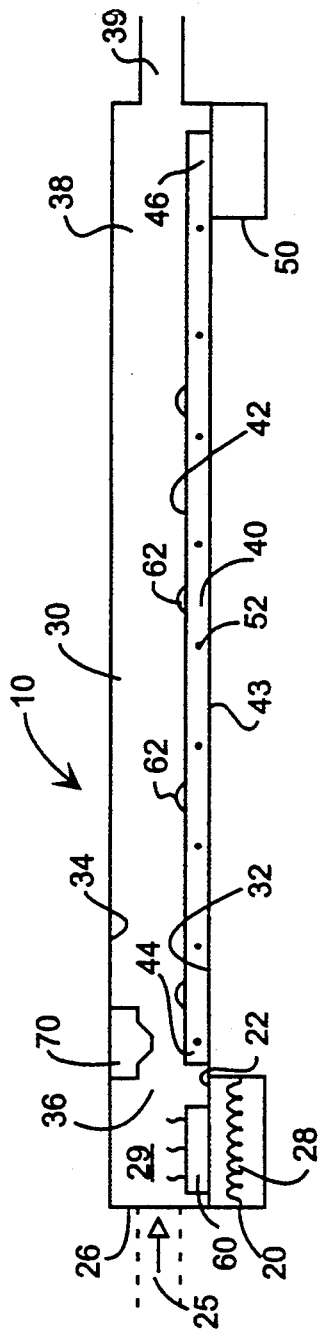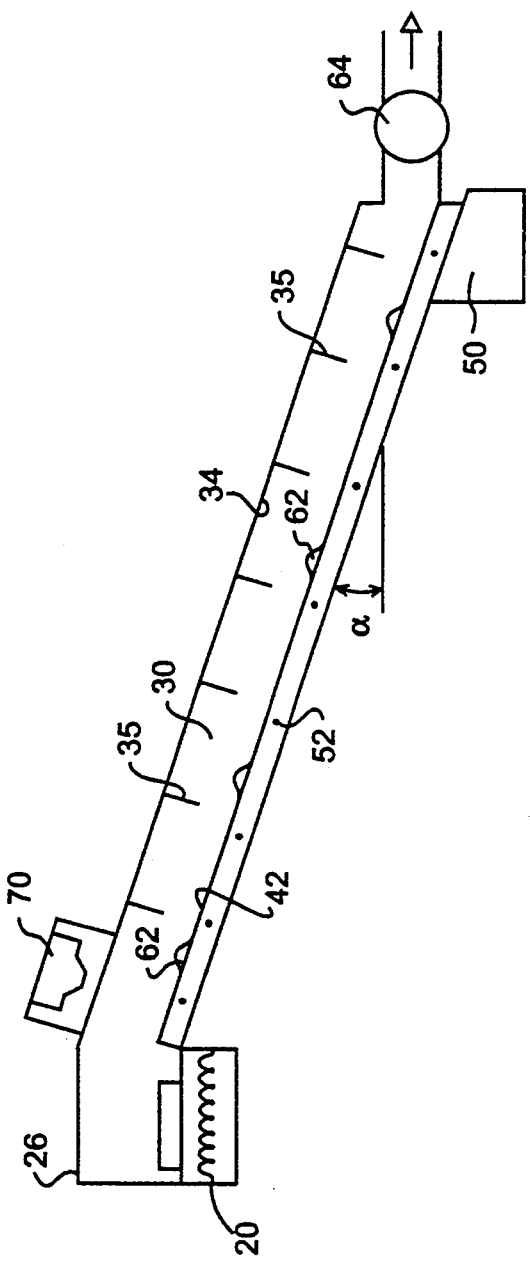

GAS EVOLUTION COMPONENT ANALYSIS

BACKGROUND OF THE INVENTION

1. Field of the Invention

The present invention relates generally to analysis of the chemical composition of the surface layers of an object. More particularly, this invention relates to a system for thermodynamically separating evolved gases to allow more effective detection and analysis thereof. Still more particularly, the present invention relates to a method and apparatus for evaporating some components from the surface of a semiconductor wafer, condensing and separating the evolved gases, and then analyzing the condensates.

2. Description of the Relevant Art

During the course of manufacturing an integrated circuit, films or layers of various substances may be applied to the surface of a silicon wafer. Some of the substances are intended to remain on the wafer surface, while others merely serve as sacraficial masking layers (photoresists), and are ultimately removed. In addition, the surface of the wafer may be doped with various substances. At some point during chip manufacture it may be desired to test the wafer and the overlying film(s), in order to ascertain both the presence of desired substances and the absence of undesired substances.

This analysis can be done by known techniques, such as infrared spectroscopy or thermogravimetric analysis (TGA). Neither technique is entirely satisfactory, however. Infrared spectroscopy is not particularly effective for detection of silicates, which have little infrared activity. Thermogravimetric analysis involves measuring the change in weight of an object as it is heated at a controlled rate, and is therefore limited in the amount of detail it can provide. For example, when used with organic materials, TGA gives insufficiently detailed information because each organic compound may fracture into two or more components, resulting in a wide range of organic molecules and making analysis of the weight data difficult. In addition, some known analytical techniques can damage the wafer, while others require destruction of the wafer.

At present, testing is often accomplished by applying heat to the wafer being tested, thereby causing some of the compounds on or near the surface of the wafer to volatilize. The resulting gas can be collected and fed into a mass spectrometer or other analytical equipment. Because many of the evolved species have similar properties, however, it is difficult to interpret the resulting spectrum. Furthermore, the gas species evolved according to this method are not monoenergetic (i.e., they show an array of energies according to a normal distribution), and therefore do not give an entirely accurate reading as they pass through the mass analyzer. Finally, only small amounts of any species are evolved, further confounding attempts at analysis.

Hence, it is desired to proved an analytical technique that allows semiconductor wafers to be effectively analyzed without destruction of the wafer. The desired technique has a minimal structural or electrical effect on the wafer and provides an easily analyzable array of the compounds present at or near the surface of the wafer.

SUMMARY OF THE INVENTION

The problems outlined above are in large part solved by a method for volatilizing two or more compounds from the surface of a wafer in a vapor mix, separating the volatilized chemicals according to their dew points and/or freezing points and then sequentially analyzing the separated chemical compounds. Even when the compounds arising from the surface of the wafer have similar physical properties, the present method allows at least partial separation and therefore permits enhanced analysis of the vapor mix. The present method comprises passing the vapor mix along a surface having a thermal gradient, with the cool end of the surface being remote from the wafer so that chemical compounds will condense sequentially along the surface according to their respective dew points. If sufficiently turbulent flow is provided, virtually all of a given chemical will condense and/or freeze before reaching the cold end of the condensing surface. Following completion of the condensation phase, the condensing surface is preferably cooled to well below the condensing temperatures, so as to minimize revolatilization of the condensate and maintain the condensed compounds on the surface. An exciter/analyzer can then be scanned along the surface of the condensing plate, allowing the condensate thereon to be analyzed incrementally. The separation afforded by sequential condensation gives greater detail than passage of the vapor mix in its entirety through a mass analyzer.

A preferred embodiment of the the present invention comprises an apparatus for analyzing chemical compounds on a surface of a body, wherein the body may include, for example, a semiconductor wafer. The apparatus includes a heater component for volatilizing the chemical compounds from the surface, a condensing surface having a hot end and a cold end, means for causing the volatilized chemical compounds to flow along the condensing surface so as to sequentially condense the chemical compounds and an exciter/analyzer for sequentially analyzing the condensed chemical compounds.

According to another embodiment, the present chemical analyzer comprises a heater component for volatilizing the chemical compounds from the surface and capturing the volatilized compounds, an inclined condensing surface having a proximal hot end and a distal cold end, a pressure drop adjacent the cold end for causing the volatilized chemical compounds to migrate along the condensing surface from the hot end to the cold end. Further according to this embodiment, the heater component and the condensing surface are sealed in a housing that includes baffles for causing turbulent gas flow adjacent the condensing surface. A scanning exciter for sequentially revolatilizing the condensed chemical compounds and an analyzer for capturing the revolatilized compounds and sequentially analyzing them are also included.

The present invention also comprises a method for analyzing chemical components at or near the surface of a semiconductor wafer. The preferred method comprises the steps of warming the wafer so as to volatilize chemical compounds at or near its surface, passing the volatilized chemical components through a condensing passage and along a condensing surface having a decreasing thermal gradient, so as to sequentially condense the chemical compounds, and exciting and analyzing the condensed chemical compounds.

BRIEF DESCRIPTION OF THE DRAWINGS

Other objects and advantages of the invention will become apparent upon reading the following detailed description and upon reference to the accompanying drawings in which:

FIG. 1 is a schematic side elevation of a preferred embodiment of the apparatus comprising the present invention; and FIG. 2 is a schematic side elevation of a second embodiment of the present apparatus.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Referring initially to FIG. 1, the analytical apparatus 10 of the present invention includes a wafer heating component 20, an optional gas flow source 25, a condensing passage 30, a cooling unit 50 and an exciter/analyzer 70. Heating component 20 preferably comprises a flat surface 22 adapted to receive a wafer 60 and includes a heater element 28. Heater element 28 can be embedded in surface 22 or positioned in close proximity to the underside of surface 22. A sealed housing 26 encloses wafer heating component 20 and condensing passage 30, forming a sealed chamber 29 over surface 22. According to a preferred embodiment, gas flow source 25 provides a steady flow of an inert carrier gas through chamber 29.

Chamber 29 feeds into condensing passage 30. Condensing passage 30 includes a floor 32, ceiling 34, and entry and exit ends 36 and 38, respectively. A cooling unit 50 is in thermal contact with floor 32 adjacent exit end 38. Passage entry 36 is preferably across chamber 29 from gas flow source 25, so that gas flowing through chamber 29 flows directly into passage 30. Passage exit 38 includes a gas flow exit 39. A vacuum pump (not shown) may also be included to allow for the evacuation of passage 30.

According to a preferred embodiment, a condensing tray 40 rests on floor 32 and extends substantially the length of passage 30. Condensing tray 40 includes an upper surface 42 and a lower surface 43. Preferably, lower surface 43 of condensing tray 40 is also in close thermal contact with floor 32, at least in the vicinity of cooling unit 50, so that heat can be effectively transferred from tray 40 through floor 32 and into cooling unit 50. Likewise, another portion of condensing tray 40 may be in thermal contact with surface 22 of heating component 20. Because cooling unit 50 is remote from heating component 20, a thermal gradient will exist along tray 40, resulting in tray 40 having a hot end 44 adjacent passage entry 36 and a cold end 46 adjacent passage exit 38. According to a preferred embodiment, a plurality of temperature measuring devices 52 (e.g., thermocouples, platinum resistance thermometers or diode thermometers) are embedded in or otherwise affixed to tray 40 between hot end 44 and cold end 46, to allow monitoring of the tray temperature at several points along its length.

In operation, a wafer 60 is placed on surface 22 with the surface to be tested directed generally upwards in an exposed position. Heat from heating element 28 passes through surface 22 and warms wafer 60, causing a mixture of gases to evolve from the surface of the wafer 60. The various compounds at or near the surface of wafer 60 volatilize at rates proportional to their respective partial pressures at the temperature to which the wafer surface is heated. Gas from gas flow source 25 carries the evolved gases into passage 30 and along condensing surface 42 of tray 40. Because the rate of evaporation of gases from the surface of wafer 60 is very low, and because it is desirable to capture as much of each species as possible, the flow of carrier gas is preferably very low. By maximizing residence time of the evolved gases in passage 30, the probability that each species will be captured on surface 42 is also maximized.

As the gases move from hot end 44 to cold end 46, higher boiling compounds condense first, followed by lower boiling ones. Preferably, cold end 46 is maintained at a temperature lower than the freezing point of the lowest-freezing compound, so that virtually all of the gas evolved from wafer 60 is condensed out of the carrier gas onto tray 40 and does not reach exit end 38. This lowest temperature may be well below room temperature, as some of the compounds evolving from the wafer may fractionate, producing secondary compounds having significantly lower freezing points.

Each species will begin to condense on tray 40 in a region where surface 42 has a temperature equal to or less than its dew point, i.e., the temperature at which its vapor pressure is less than the partial pressure of that species in the gas.

As the vapor or condensate of each species reaches the region of surface 42 at which the temperature equals its freezing point, it freezes. Condensation can occur along the length of tray 40. The various species tend to accumulate at their respective freezing points along the length of tray 40, forming a plurality of accumulations 62 on surface 42 and resulting in a separation of the species. Hence, the condensed gases are separated substantially according to their relative freezing points.

Before analyzing the condensed substances, it is preferable to evacuate the volume of gas in chamber 29 and passage 30 so that any uncondensed gases present therein will not interfere with the analysis of the condensed species. Evacuation can be achieved by closing gas flow source 25, removing the heat source from wafer heating component 20 and allowing wafer 60 to return to ambient temperature. This causes volatilization of components from the surface of wafer 60 to cease. If a continuous vacuum is to be maintained, it is preferable to decrease the overall surface temperature of tray 40 before evacuating chamber 29 and passage 30. Preferably, the temperature of surface 42 is dropped sufficiently to freeze any liquids that may be present thereon. The lower the temperature to which surface 42 is cooled, the lower the vapor pressure of the resulting solids. Thus, the solids on surface 42 will be less likely to sublime and more likely to remain on tray 40 when the passage is evacuated.

Following the evacuation step, exciter/analyzer 70 is activated and an ionizing beam, laser, or other volatilizing means is scanned along the length of tray 40. As the beam scans surface 42, the condensed materials are sequentially vaporized and drawn into a mass spectroscope (not shown). The separation of species afforded by the sequential condensation greatly facilitates analysis, even when separation of adjacent species is not complete. Hence, a more detailed and accurate assessment of the evolved species can be made, enabling better identification of the various compounds on the wafer.

It will be understood that, as an alternative to scanning exciter/analyzer 70 along surface 42, tray 40 can be moved or manipulated relative to exciter/analyzer 70, which can itself remain stationary.

Referring now to FIG. 2, several modifications of the present invention are shown included in a second embodiment. It will be understood that the modifications are not inter-related, but may be made or omitted piecemeal from the preferred embodiment described above.

In FIG. 2, a vacuum pump 64 is included at the end of passage 30. Because the vacuum source at exit end 38 of passage 30 removes any uncondensed gases and thereby reduces the pressure at exit 38, the evolved gases migrate from chamber 29 into and along passage 30 without the necessity of a carrier gas.

A second modification shown in FIG. 2 is the inclusion of baffles 35 along ceiling 34 of passage 30. Baffles 35 serve to cause turbulent gas flow in passage 30, thereby increasing the efficiency of the condensation mechanism. Baffles 35 can be configured in a variety of ways, but are preferably laterally offset from one another so as to disrupt laminar flow along surface 42.

A third modification shown in FIG. 2 is the inclination of passage 30, and specifically tray 40, at an angle α with respect to horizontal. Angle α is preferably less than 45 degrees and more preferably only a few degrees. A slight inclination of surface 42 ensures that the condensed species will not migrate or flow toward hot end 44. More preferably, they will tend to flow in accordance with gas flow and gravitation toward cold end 46. However, the liquid phase of each species will tend to encounter its freezing point well before reaching cold end 46. Thus, each species will solidify at the point where surface 42 has a temperature equal to the freezing point of that species.

A fourth modification illustrated in FIG. 2 is the retractability of exciter/analyzer 70. It will be understood that exciter/analyzer 70 can be positioned out of the direct flow line of gas through passage 30, so as to minimize condensation of gases on exciter/analyzer 70. To further decrease the likelihood of condensation at undesired points in the apparatus, housing 26 and baffles 35 may be warmed, such as by contact with an external heat source, or by the positioning of heater elements therein.

As disclosed herein, the present invention allows some separation of the constituent gases from the mix of evolved gases. Even if the separation is not complete, the present method allows general segregation of the gas species into higher-boiling and lower-boiling species, so that each species can be analyzed in a more concentrated form than is possible with simple analysis of the evolved gas mix.

Numerous other variations and modifications will become apparent to those skilled in the art once the above disclosure is fully appreciated. Thus, while a preferred embodiment of the invention has been shown and described, modifications thereof can be made by one skilled in the art without departing from the spirit of the invention. It is intended that the following claims be interpreted to embrace all such variations and modifications.

What is claimed is:

1. An apparatus for analyzing chemical compounds on a surface, comprising:
    a heater component for volatilizing the chemical compounds from the surface;
    condensing surface having a hot end and a cold end wherein said condensing surface is adapted for causing said volatilized chemical compounds to flow along said condensing surface so as to sequentially condense said chemical compounds thereon; and
    an exciter/analyzer directed toward said condensing surface for sequentially analyzing said condensed chemical compounds.

2. The apparatus of claim 1, further including means for scanning said exciter/analyzer across said condensation surface.

3. The apparatus of claim 1 wherein said exciter/analyzer includes an ion beam.

4. The apparatus of claim 1 wherein said exciter/analyzer includes a laser.

5. The apparatus of claim 1 wherein said exciter/analyzer includes a mass spectrometer.

6. The apparatus of claim 1 wherein said condensing surface is inclined.

7. The apparatus of claim 1, further including baffles for causing turbulent flow along said condensing surface.

8. The apparatus of claim 1, further including means for providing a carrier gas flow across said heated wafer and along said condensing surface, such that said carrier gas causes said volatilized chemical compounds to move across said condensing surface.

9. The apparatus of claim 1 wherein said flow-causing means comprises a vacuum pump adjacent said cold end of said condensing surface.

10. The apparatus of claim 9 wherein said condensing surface is inclined.

11. The apparatus of claim 1 wherein said surface comprises a semiconductor wafer.

12. A method for analyzing chemical components at or near the surface of a semiconductor wafer, comprising the steps of:
    warming the wafer so as to volatilize chemical compounds at or near its surface;
    passing said volatilized chemical components through a condensing passage and along a condensing surface of decreasing temperature so as to sequentially condense said chemical compounds; and
    exciting and analyzing said condensed chemical compounds.

13. The method of claim 12, further including the step of evacuating said condensing passage prior to exciting and analyzing said condensed chemical compounds.

14. The method of claim 13, further including the step of further cooling said condensing surface so as to solidify any condensate thereon prior to evacuating said condensing passage.

15. The method of claim 12, further including the step of passing an analyzer linearly across said condensing surface so as to sequentially analyze said condensate.

16. An apparatus for analyzing chemical compounds on a surface, comprising:
    a heater component for volatilizing the chemical compounds from the surface and capturing said volatilized compounds;

a declined condensing surface measured from a proximal hot end to a distal cold end;

a pressure drop adjacent said cold end for causing said volatilized chemical compounds to migrate along said condensing surface from said hot end to said cold end;

a sealed housing enclosing said heater component and said condensing surface, said housing including baffles for causing turbulent gas flow adjacent said condensing surface;

a scanning exciter for sequentially revolatilizing said condensed chemical compounds; and an analyzer for capturing said revolatilized compounds and sequentially analyzing them.

* * * * *

UNITED STATES PATENT AND TRADEMARK OFFICE
CERTIFICATE OF CORRECTION

PATENT NO. : 5,442,175
DATED : August 15, 1995
INVENTOR(S) : Robert Dawson

It is certified that error appears in the above-indentified patent and that said Letters Patent is hereby corrected as shown below:

Column 6, line 8, Claim 1, add "a" before "condensing"--.

Signed and Sealed this

Twelfth Day of December, 1995

Attest:

BRUCE LEHMAN

*Attesting Officer*  *Commissioner of Patents and Trademarks*